United States Patent [19]

Weisz

[11] 3,995,029

[45] Nov. 30, 1976

[54] METHODS FOR THE TREATMENT OF ACNE

[76] Inventor: Geraldine Fay Weisz, 2240 Harmain Road, Pittsburgh, Pa. 15235

[22] Filed: Jan. 2, 1975

[21] Appl. No.: 537,969

[52] U.S. Cl. ............................................. 424/151
[51] Int. Cl.² .................................... A61K 33/16
[58] Field of Search ........................... 424/151, 52

[56] References Cited
UNITED STATES PATENTS

| | | | |
|---|---|---|---|
| 500,549 | 7/1893 | Baekeland | 424/151 |
| 1,732,240 | 10/1929 | Menzies | 424/151 |
| 2,091,075 | 8/1937 | Landers | 424/151 |
| 2,095,464 | 10/1937 | Chesnutt, Jr. | 424/151 |
| 2,709,665 | 5/1955 | Campbell et al. | 424/151 |

OTHER PUBLICATIONS

Hopponen, Handbook of Non-Prescription Drugs, 1973 Edition, pp. 151–160, Published by the American Pharmaceutical Association.

*Primary Examiner*—Norman A. Drezin
*Attorney, Agent, or Firm*—Buell, Blenko & Ziesenheim

[57] ABSTRACT

A method and composition for treatment of acne vulgaris is provided wherein an aqueous solution of a water soluble fluoride and a surface active agent is applied to a skin area affected by acne.

5 Claims, No Drawings

METHODS FOR THE TREATMENT OF ACNE

This invention relates to methods and compositions for treatment of acne and particularly to methods and compositions for treatment of the skin disorder known as acne vulgaris.

The physical and psychological effects of acne on young persons are very well known. Moreover, there is no skin disorder which is easier to diagnose than acne, however, there are few skin disorders that are more persistent and more difficult to cure.

Acne vulgaris is a chronic inflammatory disease of the sebaceous glands and is characterized by the formation of comedones, appules and pustules on the face, neck and back. It has been suggested that acne vulgaris is a result of physiological activation of the sebaceous system, resulting from changes in the endocrine balance coincident with adolescence. Whatever the causitive process may be, the results on adolescents is well known. Inferiority complexes, backwardness and timidity in adults are frequently traced to a neglected or untreated acne of long duration in the adolescent years. Serious disfigurement of the facial skin may result from the acne or its improper treatment. While mild acne is almost expected with puberty, it is a skin disease which should not be ignored not only because of the unsightly skin condition which characterizes it but also of the possible scarring and because of the frequent long term psychological effects which it induces.

There have been many treatments proposed and used for dealing with acne vulgaris but in most cases they are too involved or too expensive or require an extraordinary degree of self discipline in the patient. For example, there have been systemic treatments proposed which depend upon the patient following a strict diet which includes the discontinuance of the use of chocolate, iodized salt, white bread, greasy and sweet foods and very rich foods. Since this is a disease primarily of adolescence and since the diet of most adolescents is very high in these very things which are proscribed, the dietary control approach is most unsatisfactory. Vaccine therapy has been suggested and in some cases is of great benefit, but it requires treatment by a physician and is not always effective. Roentgen ray treatment when properly administered is of value in many cases but it can be used only on older children and must be used wih extreme care. Moreover, people are reluctant and resistant to using this because of the danger of overexposure. Again, this treatment requires attendance of a physician and is expensive. Ultraviolet light has been suggested as a treatment and while it does appear to be of symptomatic benefit, it is not curative of the disease. It has the further drawback that it frequently produces a sunburned peeling look, often mildly painful. In addition, vast numbers of ointments, lotions, powders and the like have been proposed for the treatment of acne. Some of these are caustic and designed to cause peeling or sluffing of skin which is often painful.

I have discovered a treatment and composition which does eliminate acne vulgaris if not complicated by other physical problems.

The treatment of this invention comprises applying at regular intervals to the affected skin areas a composition consisting essentially of a water soluble fluoride, preferably sodium fluoride, and a surface active wetting agent in aqueous solution. Preferably the composition is used in a concentration such that the fluoride is present in an amount on the order of 1 grain per ounce of solution or approximtely 130 grains of fluoride per gallon of solution.

I have found by clinical tests conducted over an extended period and involving more than 100 adolescents between the ages of 14 and 18, that acne vulgaris can effectively be controlled by regular treatment according to this invention. I have found that if treatment is stopped, the acne reappears on the patient but upon resumption of treatment the acne again disappears. The only instance, in my experience with the clinical tests mentioned above, in which the acne was not cured by my treatment was a 14 year old girl who, in addition to acne problems, had a complicated menstrual disturbance.

Although I have referred specifically to the use of sodium fluoride, it should be evident that other soluble fluorides, such as stannous fluoride, potassium fluoride, etc., may be employed, provided they are in equivalent or substantially equivalent concentration in water solution.

The wetting or surface active agent constitutes a minor proportion of the composition. As such, there may be employed any of the well-known wetting agents, provided the one selected does not have any substantial effect in the direction of inactivating the fluoride. Preferably, there is employed a powdered form of wetting agent, such as one of the compounds produced and marketed by American Cyanamid and Chemical Corporation under the trade names of Aerosol AY (diamyl sodium sulfosuccinate), Aerosol IB (dibutyl sodium sulfosuccinate), and Zerosol OS (isopropylnaphthalene sodium sulfonate).

In any event, as above indicated, the surface active agent employed is one which will not react with or otherwise inactivate the soluble fluoride in the concentrations in which the surface active agent would be present when the mix is dissolved in the stated amount of water.

I have discovered, however, that anionic surfactants provide a synergistic effect in addition to the usual wetting effect and are preferred in the practice of this invention.

In general, a dry powder mix suitable for use in accordance with my invention, may be composed of the following ingredients in substantially the proportions indicated:

|  | Parts (by weight) |
| --- | --- |
| Sodium fluoride | 115 |
| Wetting agent | 0.1 |
| Sodium chloride | up to 25 |

Sodium chloride need not be present, however, I have found that its presence appears to provide a marked enhancement or synergistic effect with the fluoride when added in amounts indicated above.

A dry mix of the composition set forth above has been demonstrated to be effective when employed in aqueous solution in the concentration herein set forth, viz., such as will provide approximately one grain of the fluoride per ounce of solution. It will be understood, however, that various changes may be made in the composition without departing from the scope of the invention. Thus, as already indicated, other water soluble fluorides, such as stannous fluoride or potassium fluoride may be employed in lieu of the sodium fluoride; likewise other wetting agents, as well as scenting agents may be employed. The proportion of the wetting agent employed may vary, depending primarily upon its surface active properties and upon the particular fluoride employed and the nature of the tap water with which the dry powder mix is to be used for preparing the wash solution.

In a preferred and specific embodiment of the invention, a dry powder mix in conformity with the above-stated general formula may be compounded and packaged in individual envelopes or other suitable containers, each containing the fluoride and other ingredients in amounts as follows:

| Sodium fluoride | grains | 238 |
|---|---|---|
| Aerosol AY (wetting agent) | " | ¼ |
| Sodium chloride | " | 56 |
| Scenting agent | minims | 15 |

If desired, appropriate amounts of a suitable dye may also be added as coloring.

With envelopes containing the fluoride and other ingredients in amounts above stated, the user would be instructed, preferably by imprinting suitable directions on each envelope, to dissolve the contents thereof in one quart of distilled or pre-boiled water, and to use one tablespoonful of this solution in one-half glass of water as a wash solution, after first cleansing the face and rinsing all cleansing material from the face. The patient is also instructed to use the wash both in the morning and before retiring, by patting the wash onto the affected surface.

It will be seen that when the above-stated contents of an envelope of the dry mix are dissolved and diluted as indicated, the concentration of sodium fluoride in the final solution employed as the wash will represent about 135 grains of sodium fluoride per gallon of water, or fractionally more than one grain per ounce, and hence about 3 to 4 grains per use.

If desired, the composition of my invention may be furnished for use in the form of compressed but readily disintegratable type of tablets, each containing three grains of fluoride and proportional amounts of wetting agent and other ingredients, so that when dissolved in three to four ounces of water, it will provide a solution of the desired concentration of fluoride for use in accordance herewith.

Also, if desired, the composition may be furnished as a pre-formed solution in water, wherein the concentration of the fluoride is of the order of 135 grains per gallon.

As another alternative form, the wash solution may be packaged in the form of pre-wetted packaged gauze pads. These pads may be used to pat the solution onto the acne affected areas.

This composition may also be incorporated in soap, soap solutions or gels for application to the skin during regular washing or as a special wash for treatment purposes.

The foregoing detailed description has been given for purposes of explaining and illustrating the invention. It is accordingly to be understood that the invention is not limited to the detailed information set forth and that various modifications may be made therein without departing from the scope of the invention as defined by the appended claims.

I claim:

1. The method of alleviating acne vulgaris which comprises applying to the skin area affected by acne an effective amount of an aqueous solution of a water soluble fluoride and a surface active wetting agent of a character having no substantial effect in inactivating the fluoride, the wetting agent being present in a minor proportion relative to the fluoride and said fluoride being present in an amount effective to alleviate said acne.

2. The method as claimed in claim 1 wherein the surface active agent is an anionic surfactant.

3. The method as claimed in claim 1 wherein the fluoride is sodium fluoride.

4. The method as claimed in claim 1 wherein water soluble fluoride is present in the aqueous solution at a concentration of about 1 grain per ounce.

5. The method as claimed in claim 1 wherein sodium chloride is added in minor proportion relative to the fluoride.

* * * * *